United States Patent [19]

Kondo et al.

[11] Patent Number: 4,673,391
[45] Date of Patent: Jun. 16, 1987

[54] NON-CONTACT CONTROLLED MICROPUMP

[75] Inventors: Tatsuhei Kondo, Nagoya; Kaname Ito, Chita; Shoichiro Ikeda; Masayoshi Umeno, both of Nagoya; Kenji Ichikawa, Toki, all of Japan

[73] Assignee: Koichi Sakurai, Nishikasugai, Japan

[21] Appl. No.: 615,235

[22] Filed: May 30, 1984

[30] Foreign Application Priority Data

May 31, 1983 [JP] Japan .................................. 58-97327
Jul. 25, 1983 [JP] Japan ........................... 58-115375[U]

[51] Int. Cl.⁴ .............................................. A61M 5/00
[52] U.S. Cl. ..................................... 604/141; 604/67; 604/153; 604/246; 604/891; 128/DIG. 12
[58] Field of Search .................. 604/140, 67, 891, 30, 604/31, 33, 141, 66, 151, 153, 246, 247, 890; 128/DIG. 13, DIG. 12

[56] References Cited

U.S. PATENT DOCUMENTS

| | | |
|---|---|---|
| 3,624,821 | 11/1971 | Henderson ........................ 604/151 |
| 3,731,681 | 5/1973 | Blackshear et al. . |
| 3,951,147 | 4/1976 | Tucker et al. ...................... 604/891 |
| 4,013,074 | 3/1977 | Siposs .................................. 604/891 |
| 4,033,479 | 7/1977 | Fletcher et al. ............. 128/DIG. 12 |
| 4,077,405 | 3/1978 | Haerten et al. ............. 128/DIG. 13 |
| 4,180,074 | 12/1979 | Murry et al. ......................... 604/66 |
| 4,360,019 | 11/1982 | Portner et al. ...................... 604/891 |
| 4,443,218 | 4/1984 | DeCant, Jr. et al. ........ 128/DIG. 12 |
| 4,447,224 | 5/1984 | DeCant, Jr. et al. .................. 604/67 |
| 4,482,346 | 11/1984 | Reinicke ..................... 128/DIG. 12 |
| 4,486,190 | 12/1984 | Reinicke ................................ 604/67 |
| 4,525,165 | 6/1985 | Fischell ............................... 604/891 |
| 4,540,400 | 9/1985 | Hooven .............................. 604/247 |

FOREIGN PATENT DOCUMENTS

| | | |
|---|---|---|
| 0048423 | 3/1982 | European Pat. Off. . |
| 2306712 | 11/1976 | France . |
| 8002377 | 11/1980 | World Int. Prop. O. . |
| 1604576 | 12/1981 | United Kingdom . |
| 2119904 | 11/1983 | United Kingdom . |

OTHER PUBLICATIONS

PCT/US80/00841, Dorman, 5 Feb. 1981.
Transactions of the American Society of Artificial Internal Organs, vol. 24, 1978, pp. 229–231; P. R. Perkins et al: "Design and Initial Testing of a Totally Implantable Transcutaneously Controllable Insulin Delivery Device" p. 239, lines 9–32; FIGS. 1, 2.

*Primary Examiner*—Stephen C. Pellegrino
*Attorney, Agent, or Firm*—Oblon, Fisher, Spivak, McClelland & Maier

[57] ABSTRACT

A micropump disposed within a human body for continuously delivering small quantities of a pharmaceutical liquid stored therein to be injected in a human body, wherein the delivery rate is controlled by the action of a pharmaceutical liquid injection control device in response to external electric signals.

12 Claims, 7 Drawing Figures

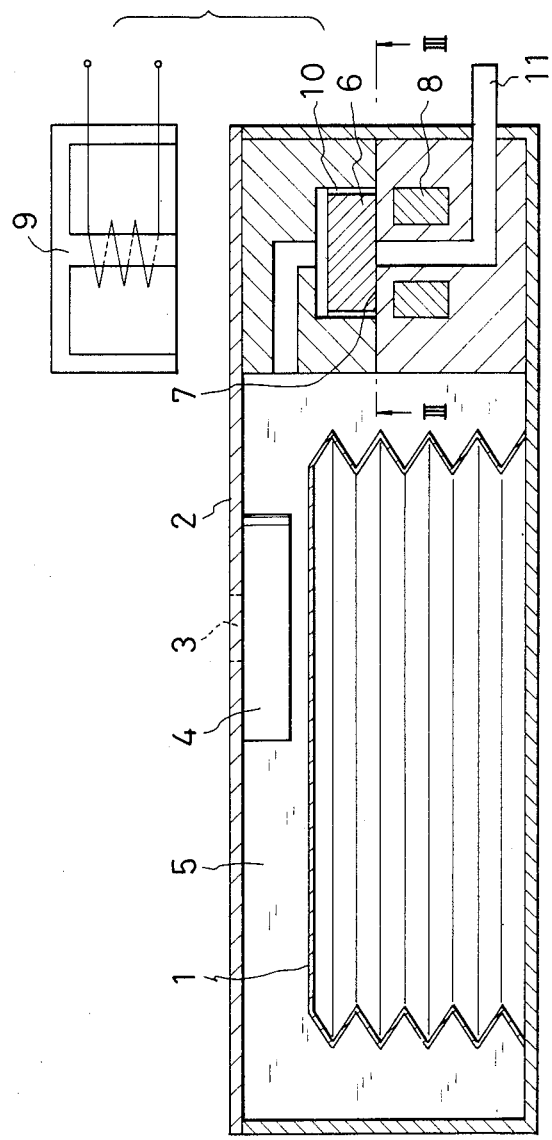

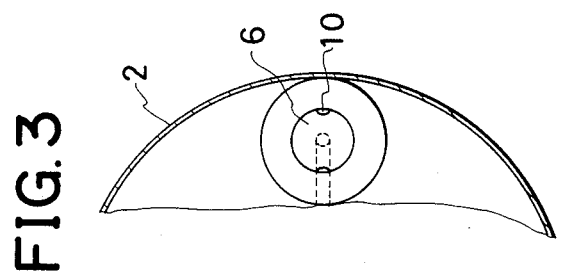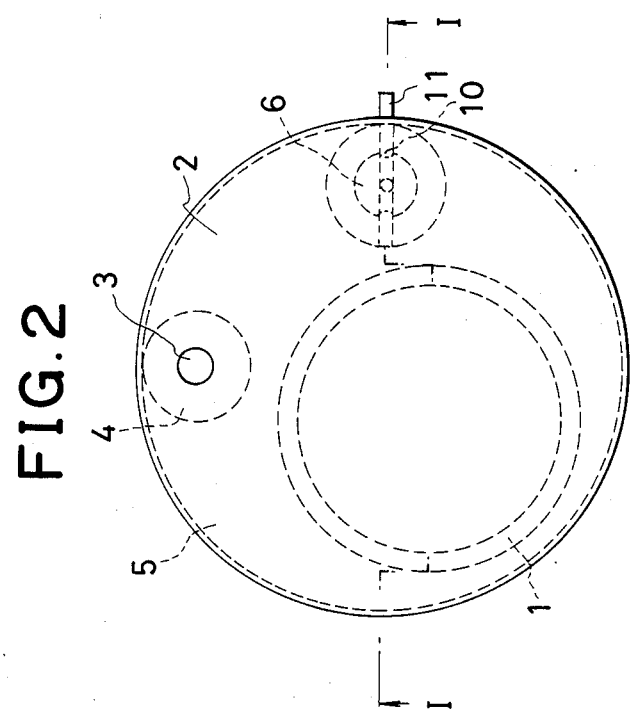

NON-CONTACT CONTROLLED MICROPUMP

BACKGROUND OF THE INVENTION

1. Field of the Invention

This invention relates to a pump having a bellows which is expanded by air, gas or vaporized gas to deliver a liquid around the bellows in small quantities, the delivery rate being remote-controlled by the action of a permanent magnet valve in response to signals of electromagnetic and more specifically, this invention relates to a micropump disposed within a human body for continuously delivering small quantities of a pharmaceutical liquid stored therein to be injected in a human body, wherein the delivery rate is controlled by the action of a pharmaceutical liquid injection control device in response to external electric signals.

2. Discussion of the Background

Generally, as a pharmaceutical liquid is injected in a day's total dose at one time, it is often excessive when injected and the major amount is rapidly drained off. As a result, the liquid amount is insufficient during the remained long time period after the dosage has been given.

SUMMARY OF THE INVENTION

The object of this invention is to provide a micropump for continuously directly delivering a pharmaceutical liquid in small quantities to a human body, in response to external electric signals, the micropump storing the dose of the pharmaceutical liquid for a number of days which is injected in a reservoir situated in a human body together, in order to avoid an imbalance in the effects of the pharmaceutical liquid.

This type of delivery system is required in various fields, particularly, for medical use in which the concentration of pharmaceuticals or essential substances in a living body should be constantly maintained. More specifically, it is essential that the delivery rate can be controlled.

For example, commonly used pharmaceuticals can remain at a constant concentration in blood if they are introduced at a constant rate. However, in order to ensure a constant concentration of glucose in blood, the insulin delivery dose must continuously be changed following the patient's moment-to-moment needs varying in accordance with the conditions in the living body.

Conventional insulin-infusion pumps, which are externally placed and designed to percutaneously inject insulin, have many problems including the risk of infection via the pierced site on the skin, and considerably restrict the patient's ordinary action.

According to this invention, the pump body is implanted in the living body, while the control part is externally placed. This eliminates the pierced site of the skin for injecting a pharmaceutical liquid and removes the risk of infection. The external control part including a power supply is small enough and light enough as compared with the conventional pump body, and is temporally detachable without problems if not for too long a period, thereby remarkably improving the patient's freedom.

According to this invention, the delivery system preferably comprises a pressure regulating valve for reducing a relatively low pressure of a pressurized liquid to a constant secondary pressure.

A more complete appreciation of the invention and many of the attendant advantages thereof will be readily obtained as the same becomes better understood by reference to the following detailed description when considered in connection with the accompanying drawings, wherein:

FIG. 1 is a sectional view taken along line I—I of FIG. 2 showing a pump of this invention;

FIG. 2 is a plan view of the pump of FIG. 1;

FIG. 3 is a sectional view taken along line III—III of FIG. 2;

DESCRIPTION OF THE PREFERRED EMBODIMENTS

Figure 4:
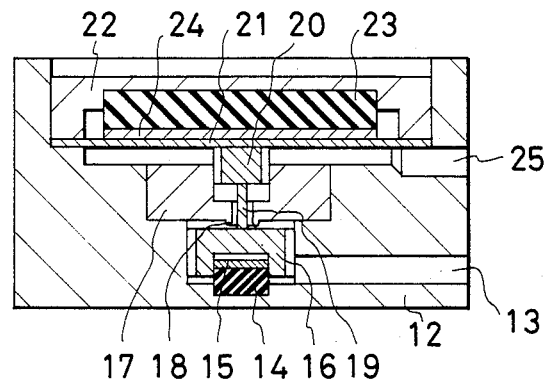
FIG. 4 is a sectional view taken along line IV—IV of FIG. 5 showing a pressure regulating valve used in the pump.

In FIGS. 1 to 3, a bellows 1 enclosing air or gas is expanded by the increase of the air, gas or vaporized gas pressure therein dependent on the body temperature. A pharmaceutical liquid is previously injected in a pharmaceutical liquid reservoir 5 via an inlet 3 of a casing 2 and a rubber packing 4 by means of an injector needle. When the bellows 1 is expanded, the pharmaceutical liquid is expelled and presses a permanent magnet valve 6 against a valve seat 7. The valve 6 is usually attracted magnetically to a ferrite core 8 to prevent the leakage of the pharmaceutical liquid. In order to open the valve 6, a stronger force of magnetic attraction is applied by an external electromagnet 9 to attract the valve 6 toward the electromagnet 9 and to keep the valve 6 apart from the valve seat 7. Then, the pharmaceutical liquid is released from a pharmaceutical liquid outlet 11 via a bypass 10 of the valve 6. When the force of magnetic attraction produced by the electromagnet 9 is cut off, the valve 6 is attracted to the ferrite core 8 to close the valve seat and to stop the release of the pharmaceutical liquid. The release dose is controlled by the time duration of the electromagnet 9.

Accordingly, the pharmaceutical liquid infusion can be externally controlled as required and at any time. More advantageously, any problems due to exhausted battery can be solved by placing a power source for controlling delivered quantities outside of the human body.

Turning now to FIGS. 4-7, illustrated is a pressure regulating valve used in the delivery system as described above.

Figure 5:
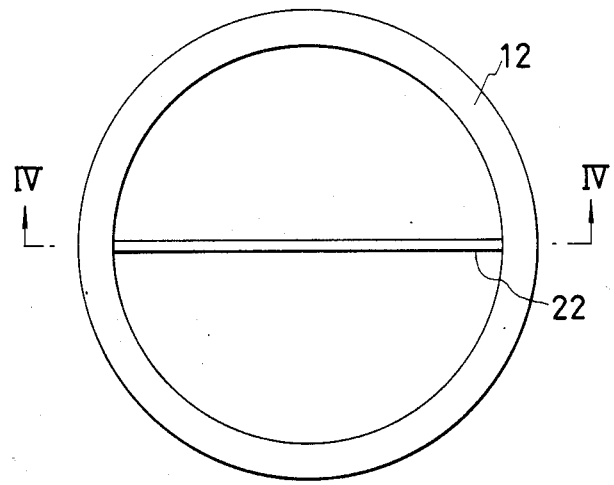
FIG. 5 is a plan view of the valve of FIG. 4.
Figure 6:
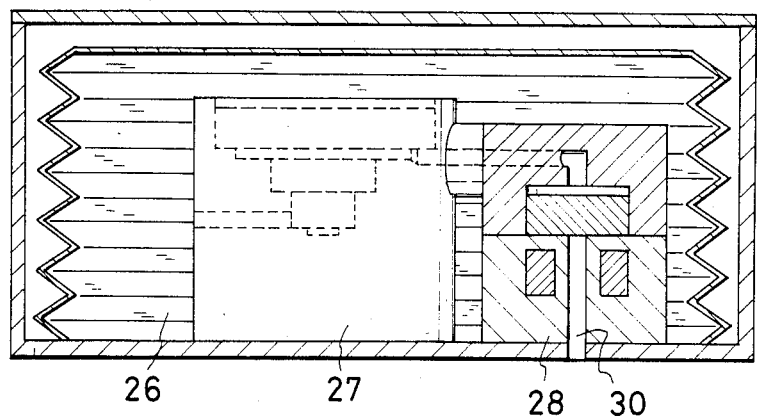
FIG. 6 is a sectional view taken along VI—VI of FIG. 7 showing an example incorporating the pressure regulating valve of FIG. 4.
Figure 7:
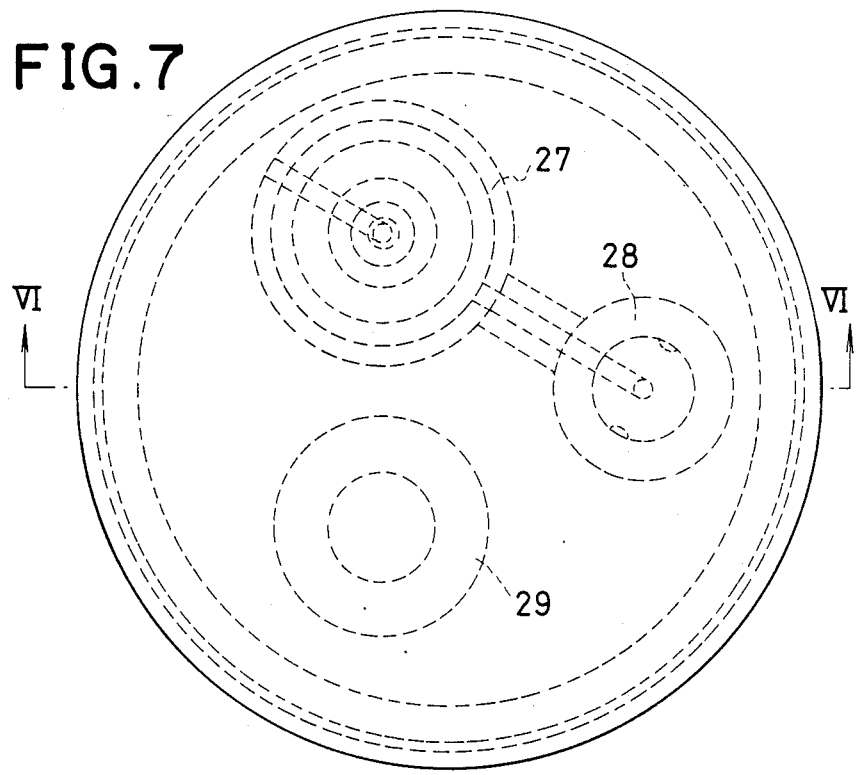
FIG. 7 is a plan view.

In order to inject a very small quantity as described above, it is necessary not only to reduce the diameter of the valve but also to limit the pressure of the pharmaceutical liquid to be injected. For this purpose, it is effective to reduce the pressure as much as possible within a tolerable limit by means of a pressure regulating valve interposed between the permanent magnet valve and the pharmaceutical liquid reservoir subjected to a gas pressure by the bellows. FIGS. 4 and 5 show a pressure regulating valve of very small type which can be used for this purpose, and FIGS. 6 and 7 show an example of application of such pressure regulating valve to a micropump.

In FIG. 4, a liquid of primary pressure enters from an inlet 13 of a body 12, and passes through a gap between the body 12 and a regulating valve 16, which is urged upward by the elastic force of a rubber member 14 and a pressure receiving plate 15, until the liquid reaches the contact region of the regulating valve 16 with a valve seat 18 of a sheet 17. The regulating valve 16 is pressed by a rod 20 driven by a diaphragm 21, said rod being connected to a needle 19 placed at the center of the valve seat. The diaphragm 21 itself receives a pressure from a pressure receiving plate 24 undergoing the elastic force of a rubber plate 23 pressed by a cover 22.

The regulating valve 16 is urged upward by the elastic force $F_1$ of the rubber plate 14 and a force $AP_1$, where $F_1$ is a small force for tightly contacting the regulating valve 16 with the valve seat 18, $P_1$ is the primary pressure and A is the area of the valve seat 18. In addition, it is assumed that the diaphragm 21 is at an initial position when the elastic force of the rubber plate 23 is adjusted so that the force thrusting the needle 19 downward under the pressure exerted on the diaphragm 21 may be equal to an upward force of the regulating valve. When the elastic force of the rubber plate 23 is slightly increased, the diaphragm 21 is moved below the initial position and the needle 19 is thrust against the regulating valve 16, thus causing the liquid of primary pressure to flow out from an outlet 25 via a gap around the needle 19 and the rod 20. When the outlet 25 is closed, the secondary pressure in the outlet is increased to move the diaphragm 21 up to the initial position. Accordingly, if the elastic force of the rubber plate 23 is adjusted in such a manner that the secondary pressure may be equal to a desired pressure $P_2$, an expected constant pressure is obtained when the outlet is closed. When the outlet 25 is slightly opened, the liquid flows out and the secondary pressure $P_2$ is decreased. Thus, the diaphragm 21 is moved downward to allow the needle to open the regulating valve so that the liquid is delivered on the secondary pressure side. The secondary pressure is now increased and the diaphragm 21 restores the initial position, thereby closing the valve seat 18 to stop the liquid inflow. In this stage, the secondary pressure comes at an expected value, since the rubber plate 23 is arranged to ensure $P_2$. Accordingly, the secondary pressure is unchanged whether the inflow is absent or at any rate.

Further, the secondary pressure is not changed even if the primary pressure is changed. The force applied to the diaphragm 21 is given by $(B-A)P_2$, where B is the area of the diaphragm 21. When the diaphragm 21 is at the initial position and all the forces are balanced, $$(B - A)P_2 = F_1 + AP_1 . \therefore P_2 = \frac{F_1}{B - A} + \frac{A}{B - A} P_1$$

As $F_1$, B and A are constants, differentiation of the pressure P gives $$\Delta P_2 = \frac{A}{B - A} \Delta P_1$$

If the valve seat has a diameter one-tenth the size of the diaphragm, A is a one-hundredth the value of of B and the variation of $P_2$ is only 1/99 of the variation of $P_1$. Accordingly, the pressure regulating valve as described above has the advantage that the secondary pressure variation can be ignored even if the primary pressure is changed.

FIGS. 6 and 7 show an example incorporating a pressure regulating valve 27 of the construction described above, as well as a pharmaceutical liquid reservoir 26, a valve 28, a pharmaceutical liquid inlet 29 and a pharmaceutical liquid outlet 30.

Obviously, numerous modifications and variations of the present invention are possible in light of the above teachings. It is therefore to be understood that within the scope of the appended claims, the invention may be practiced otherwise than as specifically described herein.

What is claimed is:

1. A micropump for delivering small quantities of a liquid, comprising:
   a casing defining a reservoir for containing the liquid,
   a first outlet provided in said casing for exhausting the liquid outside the casing,
   a bellows disposed in said casing for applying a pressure to the liquid in the reservoir,
   a first valve means positioned in said casing downstream of said inlet and electromagnetically controlled for exhausting the liquid outside the casing through said first outlet,
   pressure regulating means provided between said first valve means and said reservoir for regulating a pressure of the liquid issued to the first outlet through said first valve means, the pressure regulating means comprising a body having an inlet communicating with the reservoir, a second outlet communicating with the first valve means, a chamber communicating with said second outlet and a passage communicating said chamber with said inlet, a second valve means provided in the passage, a valve seat provided in said passage so as to be brought into contact with a surface of the second valve means and having a central bore for flowing the liquid toward the chamber, a rod movably mounted in the passage so as to open and close the central bore in cooperation with the second valve means to thereby permit and obstruct the flow of the liquid toward the chamber, a diaphragm having an area larger than that of the valve seat, mounted in the chamber so as to divide the chamber into a first chamber and a second chamber communicating with the passage and the second outlet and connected to the rod, and an elastic-force generating means disposed within the body, said elastic-force generating means generating an elastic force so that said rod is moved toward the second valve means to thereby release a contact of the second valve means with the valve seat to allow the liquid flow into the second chamber through said central bore in the case where a pressure exerted on the diaphragm in the second chamber becomes less than a predetermined pressure and so that said rod is moved toward the diaphragm to thereby keep the contact of the second valve means with the valve seat to obstruct a flow of the liquid through said central bore in the case where the pressure exerted on the diaphragm in the second chamber becomes larger than the predetermined pressure.

2. The micropump according to claim 1, in which the elastic-force generating means is attached to the second valve means.

3. The micropump according to claim 1, in which the elastic-force generating means is attached to the diaphragm.

4. The micropump according to claim 1, in which the elastic-force generating means is attached to the second valve means and the diaphragm.

5. The micropump according to claim 1, in which the elastic-force generating means further comprises means having a volume elasticity characteristic.

6. The micropump according to claim 5, in which the elastic-force generating means further comprises a rubber member.

7. The micropump according to claim 1, further comprising an electromagnet for moving said first valve means.

8. The micropump according to claim 1, which further comprises an inlet provided on the casing for introducing the liquid into the reservoir.

9. The micropump according to claim 8, in which the inlet for introducing the liquid into the reservoir further comprises injection needle means for injecting the liquid into the reservoir.

10. The micropump according to claim 8, in which the inlet for introducing the liquid into the reservoir further comprises means for percutaneously supplying pharmaceuticals.

11. The micropump according to claim 1, wherein a surface portion of the casing is formed of a biocompatible material.

12. A pump system having an electromagnet and a micropump, comprising:
a casing defining a reservoir for containing the liquid,
a first outlet provided in said casing for exhausting the liquid outside the casing,
a bellows disposed in said casing for applying a pressure on the liquid in the reservoir,
a first valve means positioned in said casing downstream of said inlet and electromagnetically controlled for exhausting the liquid outside the casing through said first outlet,
pressure regulating means provided between said first valve means and said reservoir for regulating a pressure of the liquid issued to the first outlet through said first valve means, the pressure regulating means comprising a body having an inlet communicating with the reservoir, a second outlet communicating with the first valve means, a chamber communicating with said second outlet and a passage communicating said chamber with said inlet, a second valve means provided in the passage, a valve seat provided in said passage so as to be brought into contact with a surface of the second valve means and having a central bore for flowing the liquid toward the chamber, a rod movably mounted in the passage so as to open and close the central bore in cooperation with the second valve means to thereby permit and obstruct the flow of the liquid toward the chamber, a diaphragm having an area larger than that of the valve seat, mounted in the chamber so as to divide the chamber into a first chamber and a second chamber communicating with the passage and the second outlet and connected to the rod, and an elastic-force generating means disposed within the body, said elastic-force generating means generating an elastic force so that said rod is moved toward the second valve means to thereby release a contact of the second valve means with the valve seat to flow the liquid into the second chamber through said central bore in the case where a pressure exerted on the diaphragm in the second chamber becomes less than a predetermined pressure and so that said rod is moved toward the diaphragm to thereby keep the contact of the second valve means with the valve seat to obstruct a flow of the liquid through said central bore in the case where the pressure exerted on the diaphragm in the second chamber becomes larger than the predetermined pressure, wherein said micropump is located in a human body for delivering a liquid, said electromagnet is located outside the human body, and control of said first valve means is carried out remotely by the electromagnet for adjusting the release of said liquid to the human body.

* * * * *